(12) United States Patent
Sandsten et al.

(10) Patent No.: US 11,200,697 B2
(45) Date of Patent: Dec. 14, 2021

(54) INFRARED CAMERA AMBIENT TEMPERATURE CALIBRATION SYSTEMS AND METHODS

(71) Applicant: FLIR Systems AB, Taby (SE)

(72) Inventors: Jonas Sandsten, Lomma (SE); Per Lilja, Akersberga (SE); Henning Hagman, Taby (SE); Marta Barenthin-Syberg, Stockholm (SE); Tien Nguyen, Taby (SE)

(73) Assignee: FLIR Systems AB, Täby (SE)

(*) Notice: Subject to any disclaimer, the term of this patent is extended or adjusted under 35 U.S.C. 154(b) by 0 days.

(21) Appl. No.: 16/711,149

(22) Filed: Dec. 11, 2019

(65) Prior Publication Data

US 2020/0202569 A1 Jun. 25, 2020

Related U.S. Application Data

(60) Provisional application No. 62/782,978, filed on Dec. 20, 2018.

(51) Int. Cl.
| | |
|---|---|
| *G06T 7/80* | (2017.01) |
| *G01J 5/24* | (2006.01) |
| *H04N 5/33* | (2006.01) |
| *H04N 17/00* | (2006.01) |
| *G01J 5/20* | (2006.01) |
| *G01J 5/00* | (2006.01) |

(52) U.S. Cl.
CPC .................. *G06T 7/80* (2017.01); *G01J 5/24* (2013.01); *H04N 5/33* (2013.01); *H04N 17/002* (2013.01); *G01J 2005/0048* (2013.01); *G01J 2005/0077* (2013.01); *G01J 2005/202* (2013.01); *G06T 2207/10048* (2013.01)

(58) Field of Classification Search
CPC .... G06T 7/80; G01J 5/24; H04N 5/33; H04N 17/002
See application file for complete search history.

(56) References Cited

U.S. PATENT DOCUMENTS

| | | | |
|---|---|---|---|
| 10,416,076 B2 | 9/2019 | Sandsten et al. | |
| 10,422,741 B2 | 9/2019 | Sandsten et al. | |
| 10,612,975 B2 | 4/2020 | Sandsten et al. | |
| 2004/0200961 A1* | 10/2004 | Parrish | G01J 5/522 250/338.1 |
| 2015/0369730 A1* | 12/2015 | Schmidt | G01S 17/89 250/208.1 |
| 2019/0212261 A1 | 7/2019 | Lannestedt et al. | |
| 2020/0011789 A1 | 1/2020 | Sandsten et al. | |
| 2020/0025679 A1 | 1/2020 | Nygren et al. | |
| 2020/0217719 A1* | 7/2020 | Parrish | G01J 5/54 |

* cited by examiner

*Primary Examiner* — Hugh Maupin
(74) *Attorney, Agent, or Firm* — Haynes and Boone, LLP

(57) ABSTRACT

An ambient temperature calibration process includes, in accordance with an embodiment, determining an ambient temperature calibration value for a global external resistance associated with a read out integrated circuit (ROIC) of an image capture component comprising a sensor array comprising a focal plane array of microbolometers arranged on the ROIC; determining an ambient temperature calibration value for a sensor integration time associated with the ROIC; and determining an ambient temperature calibration mapping for an offset mapping associated with the ROIC.

20 Claims, 6 Drawing Sheets

INFRARED CAMERA AMBIENT TEMPERATURE CALIBRATION SYSTEMS AND METHODS

CROSS REFERENCE TO RELATED APPLICATIONS

This application claims priority to and the benefit of U.S. Provisional Patent Application No. 62/782,978 filed Dec. 20, 2018 and entitled "INFRARED CAMERA AMBIENT TEMPERATURE CALIBRATION SYSTEMS AND METHODS," which is hereby incorporated by reference in its entirety.

TECHNICAL FIELD

One or more embodiments of the invention relate generally to infrared cameras and, more particularly for example, to calibration of microbolometer-based infrared cameras for use in variable temperature ambient conditions.

BACKGROUND

A microbolometer can be configured to detect infrared radiation. Modern microbolometer structures used for infrared imagery are typically fabricated on monolithic silicon substrates to form an array of microbolometers, with each microbolometer functioning as a pixel to produce a two-dimensional image. The change in resistance of each microbolometer is translated into a time-multiplexed electrical signal by circuitry known as the read out integrated circuit (ROIC). The combination of the ROIC and the microbolometer array is commonly known as a microbolometer focal plane array (FPA) or microbolometer infrared FPA, which are used as image capture components in infrared imaging systems.

A drawback of a conventional microbolometer FPA is that temperature changes of the microbolometer (and/or its accompanying housing and other elements of an associated infrared camera/imaging system) during the infrared radiation detection process may limit the available output signal range associated with the microbolometer and/or cause the output signal to drift, which may limit the overall performance of the microbolometer FPA. As a result, there is a need for improved techniques directed to compensating microbolometers within a microbolometer FPA and/or calibrating an infrared camera/imaging system including a microbolometer FPA, particularly in the context of gas detection/imaging.

SUMMARY

Infrared camera ambient temperature calibration systems and methods are disclosed herein in accordance with one or more embodiments of the invention. For example, systems and methods are disclosed to calibrate various parameters of an image capture component (e.g., a microbolometer FPA) used to implement an infrared imaging system/camera, which may result in a stable output signal range and improved imaging performance across a relatively wide range of ambient operating temperatures.

More specifically in accordance with one embodiment, an imaging system includes an image capture component comprising a sensor array comprising a focal plane array of microbolometers arranged on a read out integrated circuit (ROIC); and a processing component configured to communicate with the ROIC. The processing component may be configured to determine an ambient temperature calibration value for a global external resistance associated with the ROIC; determine an ambient temperature calibration value for a sensor integration time associated with the ROIC; and/or determine an ambient temperature calibration mapping for an offset mapping associated with the ROIC.

In accordance with another embodiment, a method of providing ambient temperature calibration and/or compensation for an image capture component comprising a sensor array comprising a focal plane array of microbolometers arranged on a read out integrated circuit (ROIC), includes determining an ambient temperature calibration value for a global external resistance associated with the ROIC; determining an ambient temperature calibration value for a sensor integration time associated with the ROIC; and determining an ambient temperature calibration mapping for an offset mapping associated with the ROIC.

The scope of the invention is defined by the claims, which are incorporated into this Summary by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the invention and their advantages are best understood by referring to the detailed description that follows. It should be appreciated that like reference numerals are used to identify like elements illustrated in one or more of the figures.

DETAILED DESCRIPTION

In the field of optical gas imaging (OGI), various techniques are employed to detect the presence gases. For example, specific gases may emit and/or absorb infrared (e.g. thermal) radiation in characteristic ways at particular wavelengths. Images may be captured of a scene and analyzed to determine the presence or absence of radiation at certain wavelengths. By comparing these wavelengths to the wavelengths associated with known gases, the presence of a particular gas of interest may be determined.

When a scene is imaged in accordance with such techniques, it is beneficial to stabilize the response of the imaging system used to capture the infrared spectrum wavelengths of interest, particularly with respect to ambient operating temperatures, so that level and span display tunings (e.g., with regard to displayed temperature ranges and contrast) are substantially consistent between measurements and amongst different imaging systems. In particular, embodiments provide relatively stable gas contrast output from different gas detection cameras (e.g., different infrared imaging systems and/or different image capture components).

As used herein, "gas contrast" in infrared imagery refers to the difference between (1) the presence or absence of infrared radiation at certain wavelengths associated with a known gas in an imaged scene and (2) the infrared radiation of simultaneously imaged background radiation in the imaged scene. In field operation, gas contrast is generally set by selecting, adjusting, and/or applying level and span display and/or image storage tunings to emphasize a desired range of signal/pixel intensities within an imaged scene. As long as the response of the image capture component used to capture the infrared imagery is relatively stable over a range of ambient temperatures, such level and span tunings remain substantially stable across different measurements and can be substantially consistent and stable across different infrared imaging systems and/or including different image capture components. Embodiments provide an improved approach to thermal and/or infrared-based gas imaging that, in turn, provides accurate and reliable gas detection.

Figure 1:
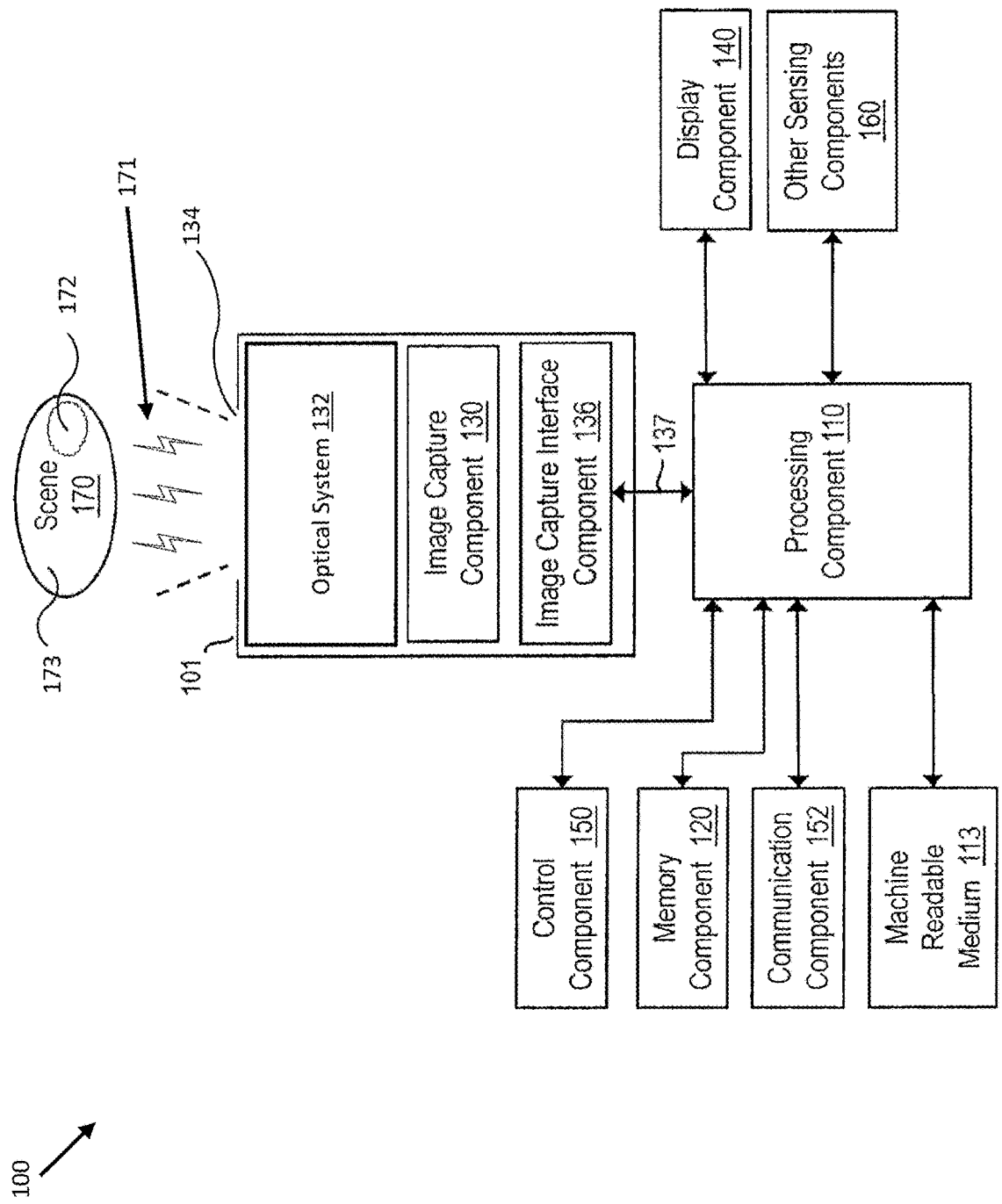
FIG. 1 illustrates a block diagram of an imaging system in accordance with an embodiment of the disclosure.

FIG. 1 illustrates a block diagram of an imaging system 100 in accordance with an embodiment of the disclosure. Imaging system 100 may be used to capture and process images in accordance with techniques described herein. In some embodiments, various components of imaging system 100 may be provided in a camera component 101, such as an infrared imaging camera. In other embodiments, one or more components of imaging system 100 may be implemented remotely from each other in a distributed fashion (e.g., networked or otherwise).

In some embodiments, imaging system 100 may be used to detect one or more gases of interest within a scene 170. For example, imaging system 100 may be configured to capture one or more images of scene 170 using camera component 101 (e.g., a thermal imaging camera) in response to infrared radiation 171 received from scene 170. Infrared radiation 171 may correspond to wavelengths that are emitted, transmitted, and/or absorbed by a gas 172 within scene 170, and other wavelengths that are emitted and/or absorbed by a background portion 173 of scene 170.

Captured images may be received by a processing component 110 and stored in a memory component 120. Processing component 110 may be configured to process the captured images in accordance with gas detection techniques discussed herein.

Figure 2:
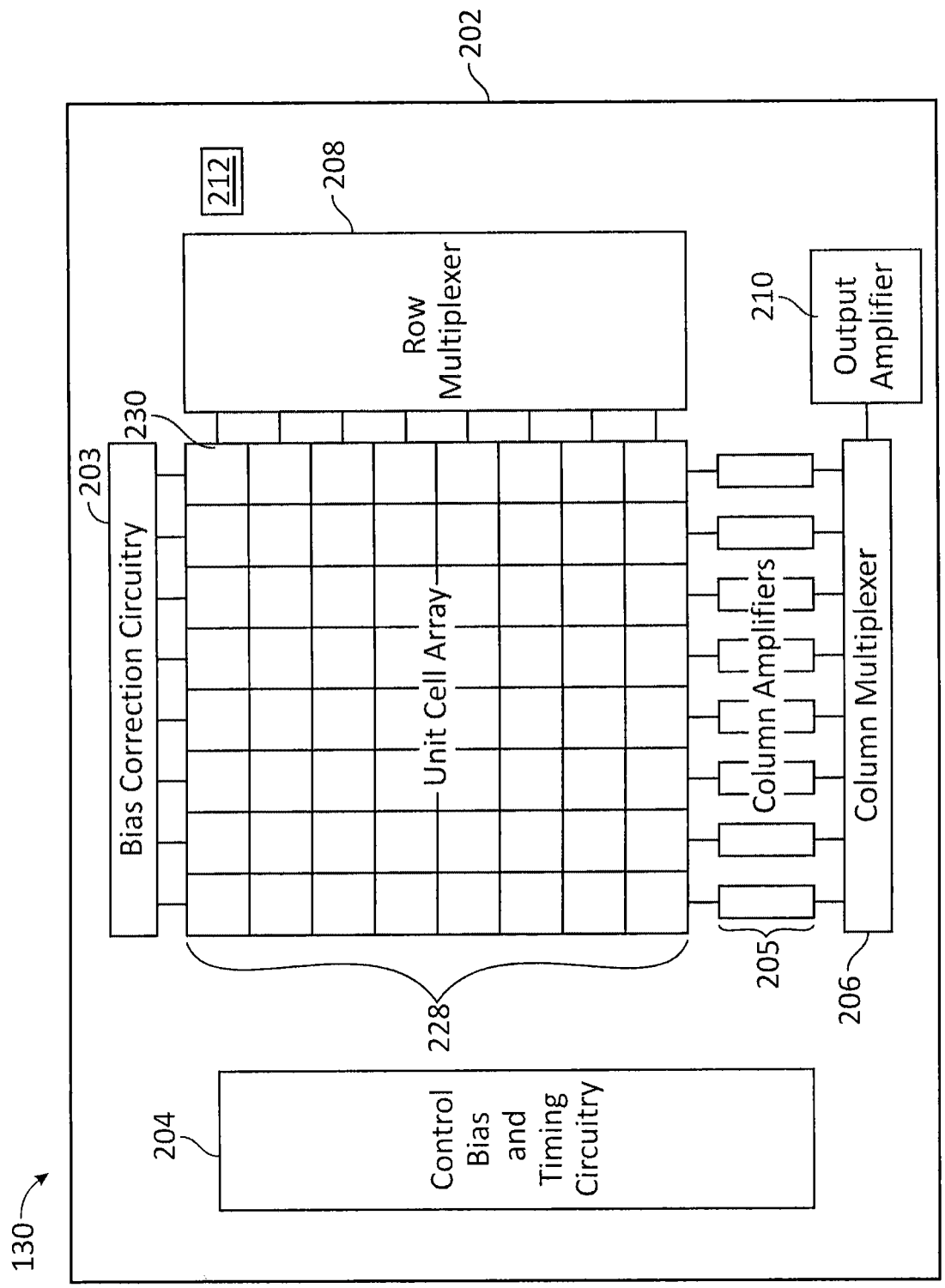
FIG. 2 illustrates a block diagram of an image capture component in accordance with an embodiment of the disclosure.

In some embodiments, imaging system 100 includes processing component 110, a machine readable medium 113, a memory component 120, image capture component 130 (e.g., including a sensor array 228 of infrared sensors 230, as shown in FIG. 2), optical system 132 (e.g., one or more lenses, shutters, filters, and/or other optical system components configured to receive infrared radiation 171 through an aperture 134 in camera component 101 and provide a corresponding infrared spectrum image to image capture component 130), an image capture interface component 136, a display component 140, a control component 150, a communication component 152, and other sensing components 160.

In some embodiments, imaging system 100 may be implemented as an imaging camera, such as camera component 101, to capture images, for example, of scene 170 (e.g., within a field of view of optical system 132/camera component 101). In some embodiments, camera component 101 may include image capture component 130, optical system 132, and image capture interface component 136 housed in a protective enclosure. Imaging system 100 may represent any type of camera system which, for example, detects electromagnetic radiation (e.g., infrared radiation 171) and provides representative data (e.g., one or more still images or video images). For example, imaging system 100 may represent a camera component 101 that is directed to detect infrared radiation and/or visible light and provide associated image data.

In some embodiments, imaging system 100 may include a portable device and may be implemented, for example, coupled to various types of vehicles (e.g., an automobile, a truck, or other land-based vehicles). Imaging system 100 may be implemented with camera component 101 at various types of fixed scenes (e.g., automobile roadway, train railway, or other scenes) via one or more types of structural mounts. In some embodiments, camera component 101 may be mounted in a stationary arrangement to capture repetitive images of scene 170.

In some embodiments, processing component 110 may include any desired type of logic circuit such as, for example, a microprocessor, a single-core processor, a multi-core processor, a microcontroller, a programmable logic device, a digital signal processing (DSP) device, one or more memories for storing executable instructions (e.g., software, firmware, or other instructions), and/or any other appropriate combinations of processing device and/or memory to execute instructions to perform any of the various operations described herein. Processing component 110 is configured to interface and communicate with the various components illustrated in FIG. 1 to perform method and processing steps as described herein. In various embodiments, it should be appreciated that processing operations and/or instructions may be integrated in software and/or hardware as part of processing component 110, or code (e.g., software or configuration data) which may be stored in memory component 120. Embodiments of processing operations and/or instructions disclosed herein may be stored by machine readable medium 113 in a non-transitory manner (e.g., a memory, a hard drive, a compact disk, a digital video disk, or a flash memory) to be executed by a computer (e.g., logic or processor-based system) to perform various methods disclosed herein.

In various embodiments, the machine readable medium 113 may be included as part of imaging system 100 and/or separate from imaging system 100, with stored instructions provided to imaging system 100 by coupling the machine readable medium 113 to imaging system 100 and/or by imaging system 100 downloading (e.g., via a wired or wireless link) the instructions from the machine readable medium (e.g., containing the non-transitory information). In various embodiments, as described herein, instructions provide for real time applications of processing various images of scene 170.

In some embodiments, memory component 120 may include one or more memory devices (e.g., one or more memories) to store data and information. The one or more memory devices may include various types of memory including volatile and non-volatile memory devices, such as RAM (Random Access Memory), ROM (Read-Only Memory), EEPROM (Electrically-Erasable Read-Only Memory), flash memory, or other types of memory. In one embodiment, processing component 110 is configured to execute software stored in memory component 120 and/or machine readable medium 113 to perform various methods, processes, and operations in a manner as described herein.

In some embodiments, image capture component 130 may include an array of sensors (e.g., any type visible light, infrared, or other type of detector) for capturing images of scene 170. In one embodiment, the sensors of image capture component 130 provide for representing (e.g., converting) captured images of scene 170 as digital data (e.g., via an analog-to-digital converter included as part of the sensor or separate from the sensor as part of imaging system 100). As further discussed herein, image capture component 130 may be implemented as an array of infrared sensors.

In some embodiments, processing component 110 may be configured to receive images from image capture component 130 over a connection 137, process the images, store the original and/or processed images in memory component 120, and/or retrieve stored images from memory component 120. In various aspects, processing component 110 may be remotely positioned, and processing component 110 may be configured to remotely receive images from image capture component 130 via wired or wireless communication with image capture interface component 136, as described herein. Processing component 110 may be configured to process images stored in memory component 120 to provide images (e.g., captured and/or processed images) to display component 140 for viewing by a user.

In some embodiments, display component 140 may include an image display device (e.g., a liquid crystal display (LCD)) or various other types of generally known video displays or monitors, including a touch screen display. Processing component 110 may be configured to display image data and information on display component 140. Processing component 110 may be configured to retrieve image data and information from memory component 120 and display any retrieved image data and information on display component 140. Display component 140 may include display electronics, which may be utilized by processing component 110 to display image data and information. Display component 140 may receive image data and information directly from image capture component 130 via processing component 110, or the image data and information may be transferred from memory component 120 via processing component 110. In various embodiments, display component 140 may be configured to display infrared images according to one or more level and span tunings, for example, to emphasize gas contrast, as described herein. Such tunings may be stored and/or retrieved from machine readable medium 113 and/or memory component 120, for example, and/or may be provided through user interaction with control component 150.

In some embodiments, control component 150 may include a user input and/or interface device having one or more user actuated components, such as one or more push buttons, slide bars, rotatable knobs or a keyboard, that are configured to generate one or more user actuated input control signals. Control component 150 may be configured to be integrated as part of display component 140 to operate as both a user input device and a display device, such as, for example, a touch screen device configured to receive input signals from a user touching different parts of the display screen. Processing component 110 may be configured to sense control input signals from control component 150 and respond to any sensed control input signals received therefrom.

In some embodiments, control component 150 may include a control panel unit (e.g., a wired or wireless handheld control unit) having one or more user-activated mechanisms (e.g., buttons, knobs, sliders, or others) configured to interface with a user and receive user input control signals. In various embodiments, it should be appreciated that the control panel unit may be configured to include one or more other user-activated mechanisms to provide various other control operations of imaging system 100, such as auto-focus, menu enable and selection, field of view (FoV), brightness, contrast, gain, offset, spatial, temporal, level and/or span, and/or various other features and/or parameters.

In some embodiments, control component 150 may include a graphical user interface (GUI), which may be integrated as part of display component 140 (e.g., a user actuated touch screen), having one or more images of the user-activated mechanisms (e.g., buttons, knobs, sliders, or others), which are configured to interface with a user and receive user input control signals via the display component 140. As an example for one or more embodiments as discussed further herein, display component 140 and control component 150 may represent appropriate portions of a tablet, a laptop computer, a desktop computer, or other type of device.

In some embodiments, processing component 110 may be configured to communicate with image capture interface component 136 (e.g., by receiving data and information from image capture component 130). Image capture interface component 136 may be configured to receive images from image capture component 130 and communicate the images to processing component 110 directly or through one or more wired or wireless communication components (e.g., represented by connection 137) in the manner of communication component 152 further described herein. Camera component 101 and processing component 110 may be positioned proximate to or remote from each other in various embodiments.

In some embodiments, imaging system 100 may include one or more other types of sensing components 160, including environmental and/or operational sensors, depending on the sensed application or implementation, which provide information to processing component 110 (e.g., by receiving sensor information from each sensing component 160). In various embodiments, other sensing components 160 may be configured to provide data and information related to environmental conditions, such as internal and/or external temperature conditions, lighting conditions (e.g., day, night, dusk, and/or dawn), humidity levels, specific weather conditions (e.g., sun, rain, and/or snow), distance (e.g., laser rangefinder), and/or whether a tunnel, a covered parking garage, or that some type of enclosure has been entered or exited. Accordingly, other sensing components 160 may include one or more conventional sensors as would be known by those skilled in the art for monitoring various conditions (e.g., environmental conditions) that may have an effect (e.g., on the image appearance) on the data provided by image capture component 130.

In some embodiments, other sensing components 160 may include devices that relay information to processing component 110 via wireless communication. For example, each sensing component 160 may be configured to receive information from a satellite, through a local broadcast (e.g., radio frequency) transmission, through a mobile or cellular network and/or through information beacons in an infrastructure (e.g., a transportation or highway information beacon infrastructure) or various other wired or wireless techniques.

In some embodiments, communication component 152 may be implemented as a network interface component (NIC) configured for communication with a network including other devices in the network. In various embodiments, communication component 152 may include one or more wired or wireless communication components, such as an Ethernet connection, a wireless local area network (WLAN) component based on the IEEE 802.11 standards, a wireless broadband component, mobile cellular component, a wireless satellite component, or various other types of wireless communication components including radio frequency (RF), microwave frequency (MWF), and/or infrared frequency (IRF) components configured for communication with a network. As such, communication component 152 may include an antenna coupled thereto for wireless communication purposes. In other embodiments, the communication component 152 may be configured to interface with a DSL (e.g., Digital Subscriber Line) modem, a PSTN (Public Switched Telephone Network) modem, an Ethernet device, and/or various other types of wired and/or wireless network communication devices configured for communication with a network.

In some embodiments, a network may be implemented as a single network or a combination of multiple networks. For example, in various embodiments, the network may include the Internet and/or one or more intranets, landline networks, wireless networks, and/or other appropriate types of communication networks. In another example, the network may include a wireless telecommunications network (e.g., cellular phone network) configured to communicate with other communication networks, such as the Internet. As such, in various embodiments, imaging system 100 and/or its individual associated components may be associated with a particular network link such as for example a URL (Uniform Resource Locator), an IP (Internet Protocol) address, and/or a mobile phone number.

FIG. 2 illustrates a block diagram of image capture component 130 in accordance with an embodiment of the disclosure. In the illustrated embodiment, image capture component 130 is implemented by a focal plane array (FPA) including a sensor array 228 of infrared sensors 230 (e.g., implemented as unit cells) and a read out integrated circuit (ROIC) 202. In various embodiments, such sensor array 228 may be referred to as a microbolometer FPA. Although an 8 by 8 array of infrared sensors 230 is shown, this is merely for purposes of example and ease of illustration. Any desired sensor array size may be used as desired.

ROIC 202 includes bias generation and timing control circuitry 204, bias correction circuitry 203, column amplifiers 205, a column multiplexer 206, a row multiplexer 208, an output amplifier 210, and a temperature sensor 212, which may be configured to measure and/or provide a temperature of a substrate of ROIC 202 and/or sensor array 228 and/or other elements of image capture component 130. Images captured by infrared sensors 230 may be provided by output amplifier 210 to processing component 110 and/or any other appropriate components to perform various processing techniques described herein.

Further descriptions of ROICs and infrared sensors (e.g., microbolometer circuits) may be found in U.S. Pat. No. 6,028,309 issued Feb. 22, 2000, which is incorporated herein by reference in its entirety.

Each infrared sensor 230 may be implemented, for example, by an infrared detector such as a microbolometer and associated circuitry to provide image data (e.g., a data value associated with a captured voltage) for a pixel of a captured image. In this regard, time-multiplexed electrical signals may be provided by the infrared sensors 230 to ROIC 202. In some embodiments, infrared sensors 230 may be implemented as gas sensors configured with a spectral response pattern including wavelengths associated with one or more gases to be detected. As a result, infrared sensors 230 may be used to provide gas pixels of gas images. Infrared sensors 230 may be operated with the same (e.g., identical) integration periods, gain settings, and readout frame rates in some embodiments. In other embodiments, these may be different for different individual infrared sensors 230.

In some embodiments, ROIC 202 may be configured to compensate for different signals received from different infrared sensors 230. For example, the resulting current signals received by ROIC 202 from infrared sensors 230 may vary in amplitude relative to each other or be otherwise disproportionate. Accordingly, in some embodiments, ROIC 202 may be configured to adjust the integration times, increase or decrease the resulting captured voltages (or other analog signal or digital value), and/or other features associated with individual infrared sensors 230 so that they may be effectively compared with each other. In some embodiments, the ROIC 202 may be implemented in accordance with any of the various configurations identified in U.S. Patent Application No. 62/446,287 filed Jan. 13, 2017, U.S. Patent Application No. 62/450,967 filed Jan. 26, 2017, U.S. Patent Application No. 62/588,878 filed Nov. 20, 2017, U.S. Patent Application No. 62/599,574 filed Dec. 15, 2017, and/or U.S. Patent Application No. 62/611,711 filed Dec. 29, 2017, all of which are incorporated herein by reference in their entirety.

Imaging system 100 may include embodiments of image capture component 130 along with control circuitry, timing circuitry, bias circuitry (e.g., including anti-ramp circuitry), row and column addressing circuitry, column amplifiers, and associated electronics to provide output signals that are digitized by an analog-to-digital (A/D) converter, which may be located as part of or separate from ROIC 202 (e.g., elements of image capture interface component 136 and/or processing component 110).

The output signals from ROIC 202 and/or such A/D converter may be adjusted by a non-uniformity correction (NUC) circuit, which applies temperature dependent compensation (e.g., Lagrange Offset, Temperature Dependent Gain, and/or additional Offset) as would be understood by one skilled in the art. After processing by such NUC circuitry, the output signals may be stored in a frame memory. The data in the frame memory is then available to display component 140 and processing component 110/memory component 120. A timing generator may be integrated with provides system timing. In various embodiments, variable circuitry such as variable resistors, digital-to-analog converters, biasing circuitry (e.g., including anti-ramp circuitry and values), which control voltage levels, biasing, circuit element values, etc., may be controlled by processing component 110 so that the output signals from ROIC 202 are substantially uniform and stable. All such circuitry may be integrated with ROIC 202, image capture interface component 136, processing component 110, and/or other elements of imaging system 100.

Figure 3:
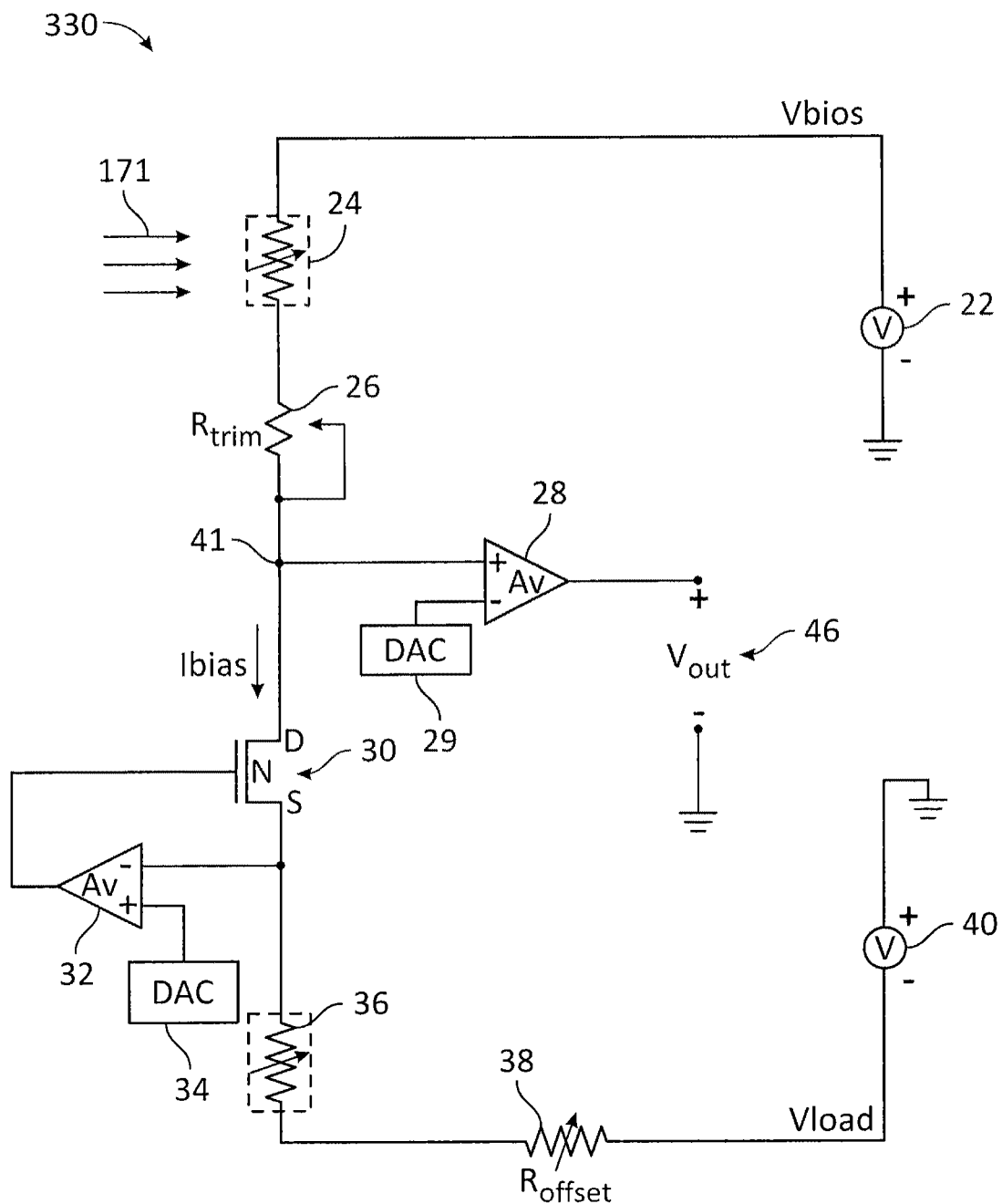
FIG. 3 illustrates an ambient temperature calibration circuit for an image capture component in accordance with an embodiment of the disclosure.

FIG. 3 illustrates an ambient temperature calibration circuit 330 for one or more infrared sensors 230 in ROIC 202 of image capture component 130, in accordance with an embodiment of the disclosure. Circuit 330 includes supply voltages 22 and 40, microbolometers 24 and 36, resistors 26 and 38, transistor 30, amplifiers 28 and 32, and digital-to-analog converters (DACs) 29 and 34. As explained in detail herein, circuit 330 may be configured to provide ambient temperature calibration for each infrared sensor 230 in ROIC 202 (e.g., including substrate temperature compensation and temperature coefficient of resistance (TCR) mismatch compensation for active and load microbolometers 24 and 36).

The active microbolometer is the thermally isolated microbolometer 24 that receives incident infrared radiation 171. Microbolometer 24 is biased by supply voltage 22 and a load current (Ibias). Amplifier 32 provides the gate bias for transistor 30 (e.g., an NMOS transistor), while DAC 34 is used to set a reference voltage and control amplifier 32 to set the appropriate gate bias for transistor 30. Alternatively, amplifier 32 can be eliminated and DAC 34 used to set the appropriate gate bias directly for transistor 30. Alternatively, DAC 34 may be replaced by a ground reference. A load circuit or bias circuit may include supply voltage 40, resistor 38, microbolometer 36, transistor 30, and amplifier 32 with DAC 34, which are used to establish the load current (Ibias).

Microbolometer 36, which is a thermally shorted (to the substrate) load microbolometer, is used as a substrate temperature compensated load. Supply voltage 40 is set to optimize the operating point for circuit 330 by setting the nominal voltage drop across microbolometer 36. In various embodiments, an output voltage (Vout) 46 of circuit 330 may be provided at a node 41, or circuit 330 may include an amplifier 28, which amplifies the voltage at node 41 to provide the output voltage (Vout) 46. Amplifier 28 is an example circuit element to provide amplification or buffering for the voltage at node 41, if desired. As with amplifier 32, a DAC 29 may provide the reference voltage (Vref) for amplifier 28 or the reference voltage may be at a set voltage level (e.g., ground). In embodiments including DAC 29, DAC 29 may be controlled to provide a varying voltage reference level for amplifier 28, for example based on a measured ambient/substrate temperature, and, thereby, an additional parameter for ambient temperature calibration and/or compensation, as described herein. It should be apparent that output voltage (Vout) 46 may be translated, amplified, or converted by amplification or integration processes and/or other signal processing techniques.

In terms of general circuit operation for circuit 330, upon application of the bias voltage Vbias by supply voltage 22 and/or 40, and as incident infrared radiation 171 levels increase, the temperature of active microbolometer 24 increases, which lowers its resistance, reduces the voltage drop across microbolometer 24, and increases the voltage level at the drain terminal of transistor 30 (i.e., node 41). This change in the voltage drop across microbolometer 24 causes a change in output voltage (Vout) 46. Therefore, as incident infrared radiation 1 levels increase or decrease, this is reflected by the voltage level of output voltage (Vout) 46 increasing or decreasing, respectively.

The length of time the bias voltage Vbias is applied to active microbolometer 24 for a particular measurement is referred to as the integration time Tint. A longer Tint provides a more sensitive sensor but narrows the range of temperatures it can measure (e.g., due at least in part to self-heating caused by Ibias, which causes the sensor to saturate).

In general, supply voltage 40 may be used to adjust the load current and thereby optimize the operating point of the circuit by setting output voltage 46 at a desired point within a range of output circuitry voltage levels. Specifically, by setting the appropriate gate bias of transistor 30 and appropriate voltage level of supply voltage 40, the output voltage (Vout) 46 is adjusted.

For example, supply voltage 40 may be a single voltage level set for the entire array of microbolometers. Amplifier 32 and DAC 34 are then used to supply a unique voltage bias to each corresponding thermally-shorted microbolometer 36 in the FPA to provide a fine adjustment or offset to the load voltage or the load current (Ibias). This corrects for the individual offset errors in the output signals from each of the thermally-isolated microbolometers (e.g., active microbolometer 24). By adjusting the offset for each microbolometer circuit, the nominal output voltage level of output voltage (Vout) 46 for each circuit may be adjusted to fall within a desired range.

To address the relative mismatch in TCR between microbolometer 24 (the active microbolometer) and microbolometer 36 (the load microbolometer), variable resistors 26 and 38 are provided. Resistor 26 is a variable resistor to generally provide fine adjustments to the composite TCR value of the active microbolometer portion of the circuit relative to the load microbolometer portion of the circuit. Thus, for the voltage divider network of resistors, resistor 26 adjusts the composite TCR of microbolometer 24 and resistor 26 relative to microbolometer 36 and resistor 38. As an example, circuit values for these circuit elements are 100 KΩ and 300 KΩ for microbolometers 24 and 36, respectively, but these values are not limiting and may vary over a large range, such as for example 50-200 KΩ and 150-600 KΩ, respectively. Exemplary circuit values for resistors 26 and 38 may, for example, vary within 0-10 KΩ and 0-30 KΩ, respectively, but this range is not limiting and may vary over a wider range of values.

Resistors 26 and 38 are typically resistors having a different TCR (generally lower) than respective microbolometers 24 and 36. For example, resistor 26 may have a low TCR and microbolometer 24 may have a higher TCR relative to microbolometer 36. Consequently, by the proper selection of resistance value for resistor 26, the combination of resistor 26 and microbolometer 24 provides a TCR that is much closer to the TCR of microbolometer 36 than is the TCR of solely microbolometer 24. Therefore, the performance and behavior of each microbolometer within the array is vastly improved over a range of substrate temperatures, which are generally at least partially dependent upon ambient temperatures, particularly with respect to uncooled FPAs.

Resistor 38 provides a coarse adjustment for circuit 330. Consequently, by setting resistor 26, temperature compensation is provided for the mismatch in relative TCR between the active microbolometer and the load microbolometer. A calibration procedure may be performed to determine the appropriate values for resistors 26 and 38. Details of an exemplary calibration procedure are provided below.

The relative mismatch in TCR is driven by various factors, such as pulse bias heating, non-uniformities among microbolometers, and relative contact resistance between the active microbolometer and the load microbolometer and the substrate. Undesirable characteristics, such as substantial ambient temperature dependence of output signals, are attributable to a certain extent to the relative mismatch in TCR between the load and active microbolometer. Ideally, by accounting for the relative mismatch in TCR and offset as a function of ambient temperature, the output voltage for a given microbolometer circuit will be well behaved (e.g., stable over a relatively wide range of temperatures).

For example, if the relative mismatch in TCR between microbolometer 24 and microbolometer 36 is such that as the substrate temperature rises, the resistance of microbolometer 24 decreases at a faster rate than microbolometer 36, output voltage 46 will increase as the ambient/substrate temperature rises for a given level of incident infrared radiation. If the measurements are repeated over the same substrate temperature range but the resistor value for resistor 26 is increased and the offset adjusted so that output value 46 is returned to the initial value for minimum substrate temperature, output voltage 46 will increase at a lower rate. This process can be repeated for various values of resistor 26 to obtain the best (e.g., most stable, or flat) response over the desired ambient/substrate temperature range. Furthermore, this procedure could be performed to obtain optimal resistor settings for each microbolometer in the array to achieve such performance.

As another example, resistor 26 and microbolometer 24 may have a lower composite TCR relative to microbolometer 36, with resistor 26 having a lower TCR than microbolometer 24. Output voltage (Vout) 46 would then have an unstable response, and the contribution of any resistance by resistor 26 would only further degrade performance due to its low relative TCR. However, by the proper selection of a resistance value for resistor 38, which has a lower TCR than microbolometer 36 (the load), the composite TCR of resistor 38 and microbolometer 36 is lower than the TCR of microbolometer 24. Thus, resistor 26 can then be set, as discussed above, to obtain the desired output response.

It should be understood that FIG. 3 is an example circuit to illustrate the relative TCR mismatch and temperature compensation techniques and that numerous modifications and variations are possible in accordance with the principles of the present invention. For example, resistor 38 may not be necessary, depending upon the characteristics of the microbolometers within the array. Resistors 26 and 38 may be implemented as parallel resistances, rather than series, relative to respective microbolometers, or some combination of series and parallel resistance may be implemented. The circuit arrangement may also vary, such as by interchanging the positions of resistor 26 and resistor 38 or the positions of microbolometer 24 and microbolometer 36. Additionally, one or more techniques discussed or referenced herein may be combined or selectively implemented, depending upon the application or various other factors.

Circuit 20 can be implemented in an array configuration, with a portion of circuit 330 placed in the unit cell while the remainder is placed outside of the unit cell, such as in column amplifiers 205. For example, microbolometer 24 may be solely placed within the unit cell (along with associated selection circuitry, such as a row select transistor that is not shown).

Figure 4:
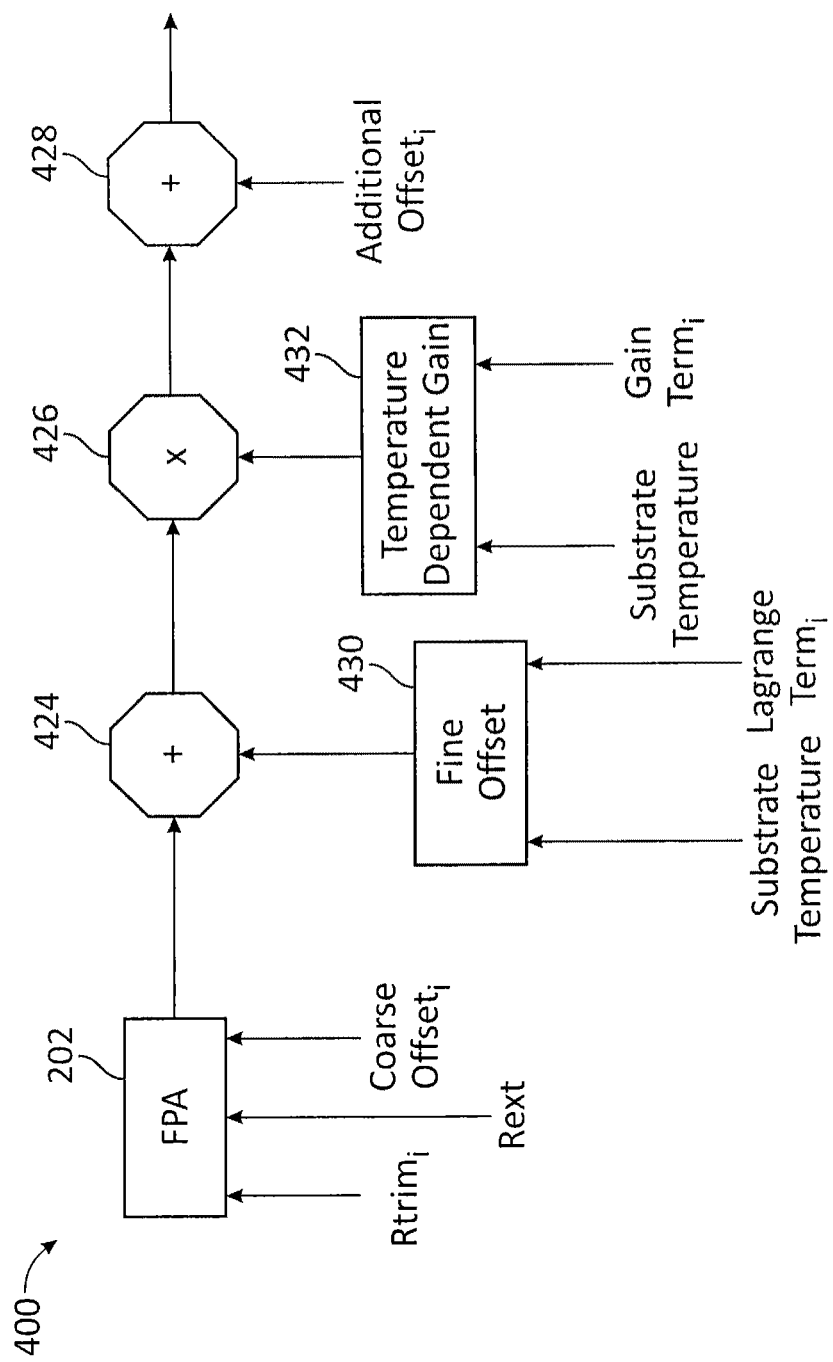
FIG. 4 illustrates a process for applying an ambient temperature calibration to an image capture component to compensate for varying ambient temperatures in accordance with an embodiment of the disclosure.

FIG. 4 illustrates a process 400 for applying an ambient temperature calibration to image capture component 130 to compensate for varying ambient temperatures in accordance with an embodiment of the disclosure. Compensation process 400 illustrates generally the overall compensation process for providing an optimal output from each microbolometer in the FPA over the desired ambient temperature range. In various embodiments, process 400 may be implemented by one or more elements of circuit 330, image capture component 130, and/or imaging system 100. A microbolometer FPA is represented symbolically by an FPA 202. As shown, each microbolometer in the array receives a trim resistor ($Rtrim_i$, where i ranges from $1 \leq i \leq$ maximum number of microbolometers in the array) and an offset calibration ($Offset_i$) adjustment. The trim resistor calibration and the offset calibration adjust each microbolometer circuit output (e.g., at node 41) over the calibrated temperature range. An external resistor (Rext) calibration value is also optionally applied, depending upon microbolometer FPA behavior. There may be an external resistor digitally selectable for each microbolometer or there may be one global external resistor that is calibrated for the entire microbolometer FPA.

The microbolometer circuit outputs from FPA 202 are combined in block 424 with the calibrated temperature-dependent fine (e.g., Lagrange) offset 430. The fine offset may be determined in any of a number of methods or techniques, as discussed herein. FIG. 4 refers to fine offset 430 as accepting Lagrange terms (e.g., a polynomial fit of calibration points across a range of temperatures), which is one exemplary method, but fine offset 430 is not intended to be limited solely to this example method. In some embodiments, fine offset 430 provides calibrated polynomial correction values for each microbolometer circuit output, which can be summed with each microbolometer circuit output from FPA 202. The microbolometer circuit outputs over the calibrated temperature range tend to produce a curved or bowed output curve, after application of the trim resistor, offset, and possibly external resistor calibrated values. The application of fine offset 430 refines the microbolometer circuit output behavior and provides a more uniform output (i.e., reduces the curve or bow in microbolometer circuit output over temperature). Fine offset 430 receives as inputs the measured ambient and/or substrate temperature and the Lagrange terms ($Lagrange\ Term_i$), which are used to generate the fine offset uniquely for each microbolometer in the array.

A block 426 receives the microbolometer circuit outputs, after application of the fine offsets, and multiplies the microbolometer circuit outputs by a corresponding calibrated temperature dependent gain 432. The gain adjusts each microbolometer circuit output to provide a more uniform response to incident flux. As shown, the gain is temperature dependent and receives as inputs the measured ambient/substrate temperature and the gain terms ($Gain\ Term_i$), which are used to generate the temperature dependent gain uniquely for each microbolometer in the array.

A block 428 receives the microbolometer circuit outputs, after application of the gain adjustment, and sums the microbolometer circuit outputs with additional offset terms ($Additional\ Offset_i$), with the additional offset for block 428 typically differing from the offset input to FPA 202. For example, the additional offset term may be updated periodically during camera operation using a shutter, a chopper, or a scene-based algorithm.

It should be appreciated that the implementation of the trim resistor within each microbolometer circuit provides the correctable microbolometer FPA performance over a wide temperature range. The correctable microbolometer FPA performance over the calibrated temperature range then permits the application of Lagrange offset, gain, and offset calibration over the wide calibrated temperature range. It should also be appreciated that the principles of this invention may be implemented or applied to a wide variety of circuit devices and materials. Accordingly, the embodiments described herein are only exemplary of the principles of the invention and are not intended to limit the invention to the specific embodiments disclosed.

Figure 5:
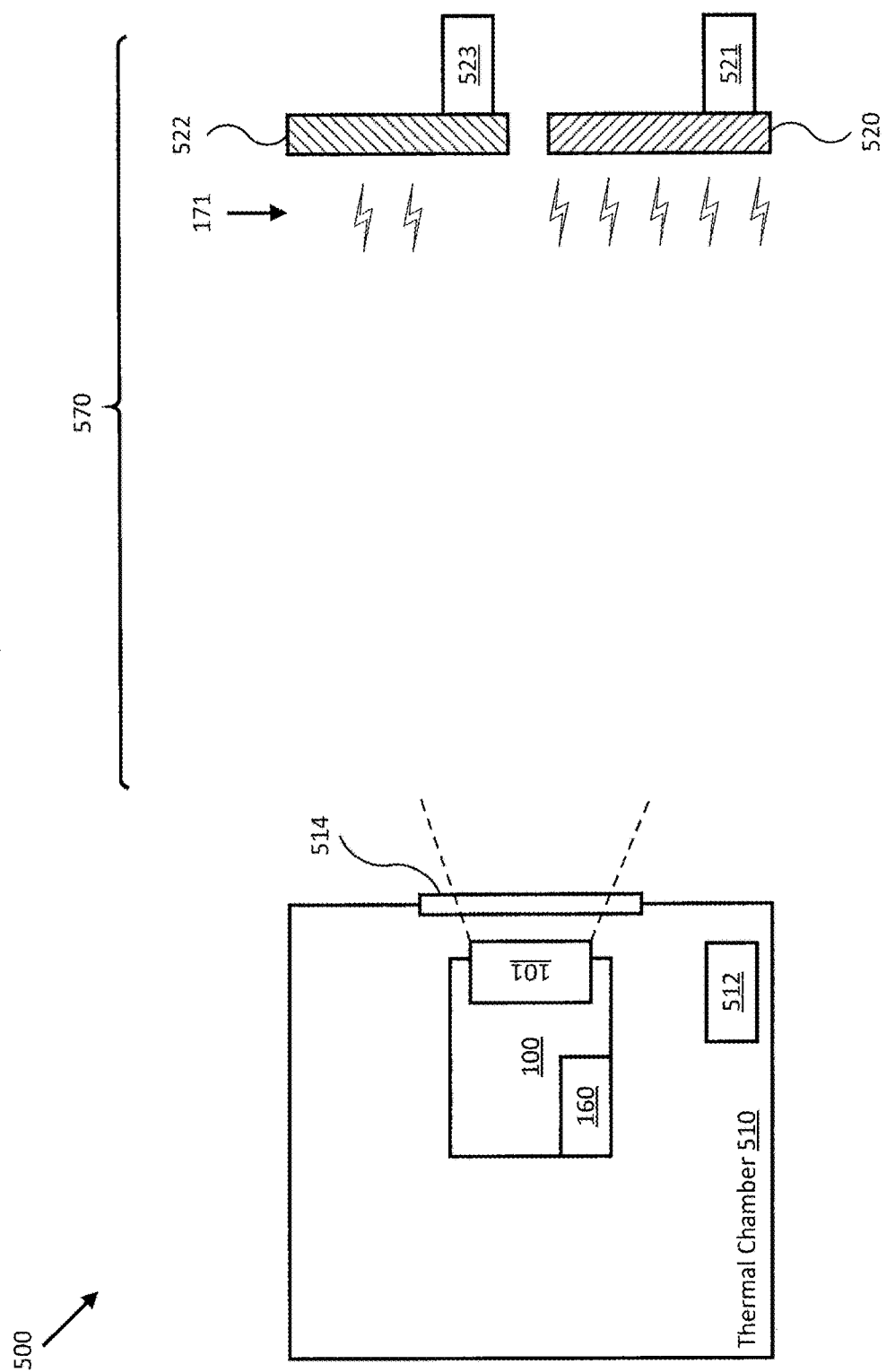
FIG. 5 illustrates a block diagram of a calibration system for an imaging system in accordance with an embodiment of the disclosure.

FIG. 5 illustrates a block diagram of a calibration system 500 for imaging system 100 in accordance with an embodiment of the disclosure. As shown in FIG. 5, calibration system 500 includes imaging system 100 placed within a temperature controlled thermal chamber 510 and oriented to view calibration scene 570 through infrared-transparent window 514 of thermal chamber 512. In some embodiments, calibration scene 570 includes one or more black body radiators 520, 521 configured to emit infrared radiation 171 detectable by image capture component 130 of camera component 101. In specific embodiments, scene 570 includes a relatively hot black body radiator 520 (e.g., warmer than ambient, a background, and/or black body radiator 522) and a relatively cold black body radiator 522 (e.g., cooler than ambient, a background, and/or black body radiator 520), both of which may be within a field of view of camera component 101/imaging system 100, such that they can be imaged substantially simultaneously.

Calibration system 500 may include various, temperature sensors 160, 512, 521, 523 configured to measure and provide temperatures of various elements of calibration system 500 and/or components of such elements, such as an enclosure, optical system, ROIC, and/or other elements of imaging system 100, thermal chamber 512, black body radiators 521 and 523, for example.

In general operation of calibration system 500, imaging system 100 is placed in thermal chamber 510 in view of calibration scene 570 through window 514.

In a first ambient temperature calibration process, an ideal ambient temperature calibration value for resistor 38/Rexp (e.g., a global external resistance for microbolometer FPA/ROIC 202) is determined. For example, during such global external resistance calibration process, the temperature of thermal chamber 500 is varied through an ambient temperature calibration range (e.g., −20 C to 50 C, −10 C to 50 C, or −20 C to 80 C) according to a series of temperature steps, at each of which thermal chamber 510 and imaging system 100 are allowed to reach thermal equilibrium and/or static relative temperatures (e.g., thermal stability, as measured by temperature sensors 512 and 160). At each temperature step, after reaching thermal stability, imaging system 100 captures a series of infrared images of calibration scene 570 while varying the global external resistance according to a set of available global external resistance values, where each infrared image includes at least a portion of relatively hot black body radiator 520 (e.g., at 100 C) and a portion of relatively cold black body radiator 522 (e.g., at 30 C) imaged simultaneously by image capture component 130 of camera component 101.

In some embodiments, an ambient temperature calibration value for the global external resistance is selected based on the stability (e.g., lack of ambient temperature dependent drift) of the pixel responses (e.g., the sampled values of Vout 46 for each sensor 230 in sensor array 228) across the ambient temperature calibration range, for each global external resistance value within the set of available global external resistance values. In other embodiments, an ambient temperature calibration value for the global external resistance is selected based on the stability of the difference between the pixel responses associated with black body radiator 520 and the pixel responses associated with black body radiator 522, across the ambient temperature calibration range. Such stabilities may be based on a selected pattern of pixels, averages of pixels, and/or other combinations of pixel responses, for example.

In some embodiments, the set of available global external resistance values is defined by a global resistance adjust (RA) number and a global active resistance adjust (RCA) number, where the RA number indicates the number of steps above zero resistance and the RCA number indicates the size of each step (e.g., generally as inputs to a digitally selectable variable resistor, which may in some embodiments be implemented by a DAC controlled transistor similar to DAC 34 and transistor 30 in circuit 330, for example, or by a plurality of resistor elements that may be variably switched into/out of a signal path using a plurality of transistors controlled by the RA and RCA numbers).

In general, the global external resistance controls the magnitude of the signal drift of Vout 46 in circuit 330 as a function of ambient temperature, where an increased global external resistance generally reduces such drift, up to a point where Vout 46 of circuit 330 becomes saturated (e.g., where active microbolometer 24 no longer tracks infrared radiation 171 and/or the temperatures of black body radiators 520 and/or 522). In various embodiments, it can be advantageous to maximize the available global external resistance (e.g., generally specific to each type of ROIC 202), such as by selecting the largest available RA number and largest available RCA number. The ambient temperature calibration value for the global external resistance can be set for multiple FPAs of the same type, for example, or may be set for each individual FPA/image capture component 130. One example selected RA and RCA pair for a microbolometer FPA is 63 and 1, respectively.

In a second ambient temperature calibration process, an ideal ambient temperature calibration value for the integration time Tint is determined. For example, during such Tint calibration process, the temperature of thermal chamber 500 is varied through an ambient temperature calibration range according to a series of temperature steps, at each of which thermal chamber 510 and imaging system 100 are allowed to reach thermal stability. At each temperature step, after reaching thermal stability, imaging system 100 captures a series of infrared images of calibration scene 570 while varying Tint across a range of available integration times, where each infrared image includes at least a portion of relatively hot black body radiator 520 and a portion of relatively cold black body radiator 522 imaged simultaneously by image capture component 130 of camera component 101.

In some embodiments, an ambient temperature calibration value for Tint is selected based on the stability (e.g., lack of ambient temperature dependent drift) of the pixel responses across the ambient temperature calibration range, for example, and/or based on a desired pixel response associated with each of black body radiator 520 and 522, for each Tint across the range of available integration times, across the ambient temperature calibration range. In other embodiments, an ambient temperature calibration value for Tint is selected based on the stability of the difference between the pixel responses associated with black body radiator 520 and the pixel responses associated with black body radiator 522, and/or a desired difference between the pixel responses associated with black body radiator 520 and the pixel responses associated with black body radiator 522, across the ambient temperature calibration range.

Such desired pixel responses may be selected and/or used to calibrate the sensitivity and measurement saturation of a number of different imaging systems 100 to each other, for example. The ambient temperature calibration value for Tint is generally set for each individual FPA/image capture component 130. One example Tint for a microbolometer FPA and a thermographic optimized optical system 132 is 18-22 us, and another example Tint for a microbolometer FPA and a methane gas detection optimized optical system 132 is 59 us.

In a third ambient temperature calibration process, an ideal ambient temperature calibration mapping of gate biases for transistor 30, resistance values for resistor 26/Rtrim, reference voltages for amplifier 28, and/or fine offset terms for fine offset block 430, which may be defined as a function of ambient temperature (e.g., coarse and fine signal offset mappings associated with each output signal Vout 46 for each sensor 230 of array 228) are determined. For example, during such offset calibration process, the temperature of thermal chamber 500 is varied through an ambient temperature calibration range according to a series of temperature steps, at each of which thermal chamber 510 and imaging system 100 are allowed to reach thermal stability.

At each temperature step, after reaching thermal stability, imaging system 100 captures a series of infrared images of a single black body radiator 522 (e.g., at 35 C) of calibration scene 570 (e.g., imaged by all sensors 230 of array 228) while varying the coarse offset (e.g., the gate bias for transistor 30) according to a set of available coarse offset values, for each sensor 230 of array 228 (e.g., to form a corresponding series of per-pixel coarse offsets/coarse offset mappings).

In some embodiments, an ambient temperature calibration mapping for the coarse offset mapping is selected based on the stability (e.g., lack of ambient temperature dependent variability) of each pixel response associated with black body radiator 520 across the ambient temperature calibration range applied to imaging system 100, for each coarse offset value within the set of available coarse offset values.

In some embodiments, the set of available coarse offset values is defined by a coarse offset adjustment (RM) number, where the RM number is proportional to the gate bias applied to transistor 30 (e.g., as generated by DAC 34 and/or amplifier 32 of circuit 330). In other embodiments, the set of available coarse offset values is at least partially defined by resistance values for resistor 26/Rtrim (e.g., selected similarly to RA/RCA for the global external resistance, but per pixel) and/or reference voltages for amplifier 28 (e.g., selected similarly to RM for the gate bias applied to transistor 30). Each of such parameters may be varied individually using a similar process to maximize stability of each pixel response associated with black body radiator 520 across the ambient temperature calibration range applied to imaging system 100, as described herein.

In various embodiments, the selection of each particular coarse offset and/or other related parameter may also be based on the available variability of a fine offset that may be applied to the same pixel, so that any remaining ambient temperature variability is substantially within the available variability of the fine offset.

For example, in some embodiments, the set of available fine offset values is defined by a offset adjust (OA) number and an offset range adjustment (ORA) number, where the OA number is proportional to the fine signal offset added to Vout 46 and indicates the number of steps above zero fine signal offset, and where the ORA number indicates the size of each step (e.g., generally as inputs to a digitally applied final signal offset). As such, the value of each particular coarse offset and/or other related parameter may be selected to ensure the associated ambient temperature dependent pixel response variability, after application of one or more of the various ambient temperature calibration values and/or mappings described above, is within the range of the available fine offset.

Upon selection of a coarse offset mapping, the temperature of thermal chamber 500 is varied through the ambient temperature calibration range a second time. At each temperature step, after reaching thermal stability, imaging system 100 captures a series of infrared images of black body radiator 520 of calibration scene 570 (e.g., imaged by all sensors 230 of array 228) while varying the fine offset term according to a set of available fine offset values, for each sensor 230 of array 228 (e.g., to form a corresponding series of per-pixel fine offsets/fine offset mappings).

In various embodiments, an ambient temperature calibration mapping for the fine offset mapping is selected based on the stability (e.g., lack of ambient temperature dependent variability) of each pixel response associated with black body radiator 520 across the ambient temperature calibration range applied to imaging system 100, for each fine offset value within the set of available fine offset values. In alternative embodiments, the set of available fine offset values is at least partially defined by resistance values for resistor 26/Rtrim (e.g., selected similarly to RA/RCA for the global external resistance, but per pixel) and/or reference voltages for amplifier 28 (e.g., selected similarly to RM for the gate bias applied to transistor 30). Each of such parameters may be varied individually using a similar process to maximize stability of each pixel response associated with black body radiator 520 across the ambient temperature calibration range applied to imaging system 100, as described herein.

The various components of the ambient temperature calibration mapping for the offset signal mappings can be set for multiple FPAs of the same type, for example, or may be set for each individual FPA/image capture component 130. One example RM range for a microbolometer FPA is 29-33. Typically, an RM mapping is set for each individual image capture component 130. One example selected OA and ORA pair is 8-24 and 2, respectively. Typically, ORA is set for multiple FPAs or image capture components 130 of the same type, and an OA mapping is set for each individual image capture component 130 and includes multiple temperature dependent OA maps.

Figure 6:
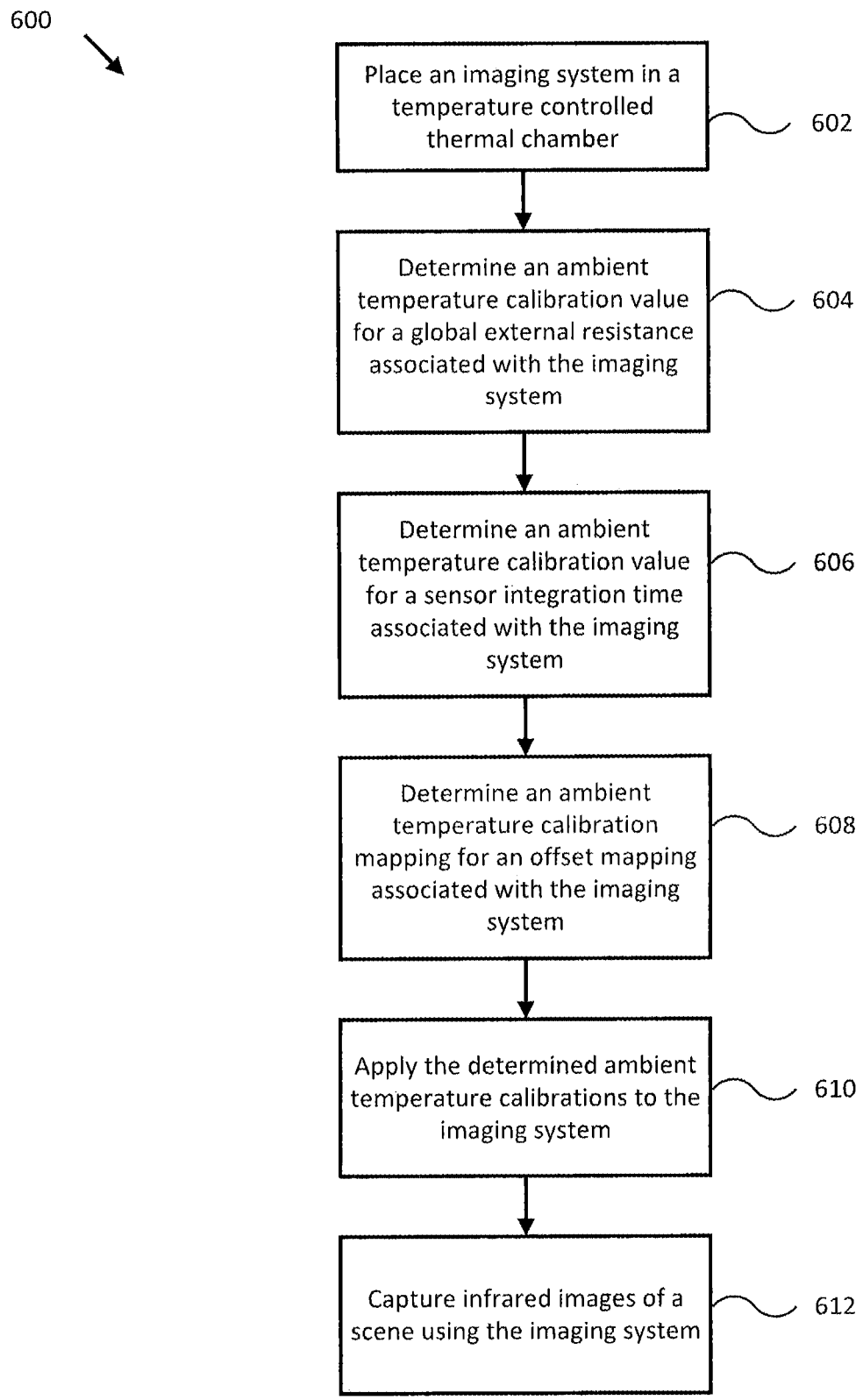
FIG. 6 illustrates a flow diagram for an ambient temperature calibration process for an imaging system in accordance with an embodiment of the disclosure.

FIG. 6 illustrates a flow diagram of an ambient temperature calibration process 600 to generate an ambient temperature calibration for image capture component 130 of imaging system 100 in accordance with an embodiment of the disclosure. It should be appreciated that any step, sub-step, sub-process, or block of process 600 may be performed in an order or arrangement different from the embodiments illustrated by FIG. 6. For example, in other embodiments, one or more blocks may be omitted from or added to the process. Furthermore, block inputs, block outputs, various sensor signals, sensor information, calibration parameters, and/or other operational parameters may be stored to one or more memories prior to moving to a following portion of a corresponding process. Although process 600 is described with reference to systems and processes described in reference to FIGS. 1-5, process 600 may be performed by other systems different from those systems and processes and including a different selection of electronic devices, sensors, assemblies, and/or other elements or components, for example.

In block 602, imaging system 100 is placed within temperature controlled thermal chamber 510 of calibration system 500. In block 604, an ambient temperature calibration value for a global external resistance associated with imaging system 100 is determined. For example, processing component 110 may be configured to determine a global external resistance associated with resistor 38/Rexp of circuit 330 that stabilizes pixel responses while image capture component 130 images calibration scene 570 across an ambient temperature range applied to imaging system 100 by thermal chamber 510, in a first ambient temperature calibration process, as described herein.

In block 606, an ambient temperature calibration value for a sensor integration time Tint associated with imaging system 100 is determined. For example, processing component 110 may be configured to determine a Tint associated with sensor array 228 that stabilizes pixel responses and/or produces desired pixel responses while image capture component 130 images calibration scene 570 across an ambient temperature range applied to imaging system 100 by thermal chamber 510, in a second ambient temperature calibration process, as described herein. In block 608, an ambient temperature calibration mapping for an offset mapping associated with imaging system 100 is determined. For example, processing component 110 may be configured to determine coarse and/or fine offset mappings associated with sensor array 228 that stabilizes pixel responses while image capture component 130 images calibration scene 570 across an ambient temperature range applied to imaging system 100 by thermal chamber 510, in a third ambient temperature calibration process, as described herein.

In block 610, one or more ambient temperature calibrations are applied to imaging system 100. For example, associated with imaging system 100 is determined. For example, processing component 110 may be configured to apply the ambient temperature calibration value for the global external resistance determined in block 604, the ambient temperature calibration value for sensor integration time Tint determined in block 606, and/or the ambient temperature calibration mapping for the offset mapping determined in block 608 to image capture component 130 of imaging system 100. In block 612, infrared images of scene 170 are captured. For example, processing component 110 and/or other elements of imaging system 100 may be configured to control camera component 101 of imaging system 100 to capture one or more infrared spectrum images of scene 170 including infrared radiation 171 associated with gas 172 and/or background portion 173 of scene 170.

Embodiments can thereby provide reliable and accurate ambient temperature calibration for imaging systems implemented by one or more microbolometer based FPAs, ROICs, and/or other image capture components, as described herein.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as non-transitory instructions, program code, and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into substeps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed is:

1. An imaging system comprising:
   an image capture component comprising a sensor array comprising a focal plane array of microbolometers arranged on a read out integrated circuit (ROIC); and
   a processing component configured to communicate with the ROIC, wherein the processing component is configured to:
      determine an ambient temperature calibration value for a global external resistance associated with the ROIC;
      determine an ambient temperature calibration value for a sensor integration time associated with the ROIC; and
      determine an ambient temperature calibration mapping for an offset mapping associated with the ROIC.

2. The imaging system of claim 1, wherein the processing component is configured to:
   apply one or more of the ambient temperature calibration value for the global external resistance, the ambient temperature calibration value for the sensor integration time, and the ambient temperature calibration mapping for the offset mapping to the ROIC; and
   control the ROIC to capture one or more infrared images of a scene including infrared radiation associated with a gas and a background portion of the scene.

3. The imaging system of claim 1, wherein the determining the ambient temperature calibration value for the global external resistance comprises:
   controlling the image capture component to capture a series of infrared images of a calibration scene while varying the global external resistance according to a set of available global external resistance values, where each infrared image includes at least a portion of a relatively hot black body radiator and a portion of a relatively cold black body radiator; and
   selecting the ambient temperature calibration value for the global external resistance based on a stability of pixel responses across an ambient temperature range, for each global external resistance value within the set of available global external resistance values; or
   selecting the ambient temperature calibration value for the global external resistance based on a stability of differences between pixel responses associated with the relatively hot black body radiator and pixel responses associated with the relatively cold black body radiator, across the ambient temperature calibration range, for each global external resistance value within the set of available global external resistance values.

4. The imaging system of claim 1, wherein the determining the ambient temperature calibration value for the sensor integration time comprises:
   controlling the image capture component to capture a series of infrared images of a calibration scene while varying the sensor integration time across a range of available integration times, where each infrared image includes at least a portion of a relatively hot black body radiator and a portion of a relatively cold black body radiator; and
   selecting the ambient temperature calibration value for the sensor integration time based on a stability of pixel responses across an ambient temperature range and/or based on a desired pixel response associated with each black body radiator across the ambient temperature calibration range, for each sensor integration time across the range of available integration times; or selecting the ambient temperature calibration value for the sensor integration time based on a stability of differences between pixel responses associated with the relatively hot black body radiator and pixel responses associated with the relatively cold black body radiator, and/or a desired difference between the pixel responses associated with the relatively hot black body radiator and the pixel responses associated with the relatively cold black body radiator, across the ambient temperature calibration range, for each sensor integration time across the range of available integration times.

5. The imaging system of claim 1, wherein the determining the ambient temperature calibration mapping for the offset mapping comprises:
controlling the image capture component to capture a series of infrared images of a calibration scene, where each infrared image includes a single black body radiator;
selecting a coarse offset mapping component of the offset mapping based, at least in part, on a stability of each pixel response associated with the single black body radiator, across an ambient temperature range applied to the imaging system, for each coarse offset value within a set of available coarse offset values; and
selecting a fine offset mapping component of the offset mapping based on a stability of each pixel response associated with the single black body radiator, across an ambient temperature range applied to the imaging system, for each fine offset value within a set of available fine offset values.

6. The imaging system of claim 1, wherein the ROIC comprises, for each sensor in the sensor array:
an active microbolometer and a load microbolometer; and
a transistor coupled between the active microbolometer and the load microbolometer and between the load microbolometer and an output node of the sensor;
wherein the processing component is configured to control the transistor to provide, at least in part, a coarse offset for the sensor.

7. The imaging system of claim 1, wherein the ROIC comprises:
for each sensor in the sensor array, an active microbolometer and a load microbolometer; and
a variable resistor coupled between the active microbolometer and the load microbolometer and between the load microbolometer and an output node of the sensor;
wherein the processing component is configured to control the variable resistor to provide, at least in part, a global external resistance for the ROIC.

8. The imaging system of claim 1, wherein the processing component is configured to:
for each sensor in the sensor array, apply a fine offset value of a fine offset mapping to an output signal of the sensor, wherein the fine offset value and/or the fine offset mapping are ambient temperature dependent.

9. A method of providing ambient temperature calibration and/or compensation for an image capture component comprising a sensor array comprising a focal plane array of microbolometers arranged on a read out integrated circuit (ROIC), the method comprising:
determining an ambient temperature calibration value for a global external resistance associated with the ROIC;
determining an ambient temperature calibration value for a sensor integration time associated with the ROIC; and
determining an ambient temperature calibration mapping for an offset mapping associated with the ROIC.

10. The method of claim 9, further comprising:
applying one or more of the ambient temperature calibration value for the global external resistance, the ambient temperature calibration value for the sensor integration time, and the ambient temperature calibration mapping for the offset mapping to the ROIC; and
controlling the ROIC to capture one or more infrared images of a scene including infrared radiation associated with a gas and a background portion of the scene.

11. The method of claim 9, wherein the determining the ambient temperature calibration value for the global external resistance comprises:
controlling the image capture component to capture a series of infrared images of a calibration scene while varying the global external resistance according to a set of available global external resistance values, where each infrared image includes at least a portion of a relatively hot black body radiator and a portion of a relatively cold black body radiator; and
selecting the ambient temperature calibration value for the global external resistance based on a stability of pixel responses across an ambient temperature range, for each global external resistance value within the set of available global external resistance values.

12. The method of claim 9, wherein the determining the ambient temperature calibration value for the global external resistance comprises:
controlling the image capture component to capture a series of infrared images of a calibration scene while varying the global external resistance according to a set of available global external resistance values, where each infrared image includes at least a portion of a relatively hot black body radiator and a portion of a relatively cold black body radiator; and
selecting the ambient temperature calibration value for the global external resistance based on a stability of differences between pixel responses associated with the relatively hot black body radiator and pixel responses associated with the relatively cold black body radiator, across the ambient temperature calibration range, for each global external resistance value within the set of available global external resistance values.

13. The method of claim 9, wherein the determining the ambient temperature calibration value for the sensor integration time comprises:
controlling the image capture component to capture a series of infrared images of a calibration scene while varying the sensor integration time across a range of available integration times, where each infrared image includes at least a portion of a relatively hot black body radiator and a portion of a relatively cold black body radiator; and
selecting the ambient temperature calibration value for the sensor integration time based on a stability of pixel responses across an ambient temperature range and/or based on a desired pixel response associated with each black body radiator across the ambient temperature calibration range, for each sensor integration time across the range of available integration times.

14. The method of claim 9, wherein the determining the ambient temperature calibration value for the sensor integration time comprises:
controlling the image capture component to capture a series of infrared images of a calibration scene while varying the sensor integration time across a range of available integration times, where each infrared image includes at least a portion of a relatively hot black body radiator and a portion of a relatively cold black body radiator; and selecting the ambient temperature calibration value for the sensor integration time based on a stability of differences between pixel responses associated with the relatively hot black body radiator and pixel responses associated with the relatively cold black body radiator, and/or a desired difference between the pixel responses associated with the relatively hot black body radiator and the pixel responses associated with the relatively cold black body radiator, across the ambient temperature calibration range, for each sensor integration time across the range of available integration times.

15. The method of claim 9, wherein the determining the ambient temperature calibration mapping for the offset mapping comprises:

controlling the image capture component to capture a series of infrared images of a calibration scene, where each infrared image includes a single black body radiator;

selecting a coarse offset mapping component of the offset mapping based, at least in part, on a stability of each pixel response associated with the single black body radiator, across an ambient temperature range applied to the imaging system, for each coarse offset value within a set of available coarse offset values; and selecting a fine offset mapping component of the offset mapping based on a stability of each pixel response associated with the single black body radiator, across an ambient temperature range applied to the imaging system, for each fine offset value within a set of available fine offset values.

16. The method of claim 9, wherein the ROIC comprises, for each sensor in the sensor array:

an active microbolometer and a load microbolometer; and a transistor coupled between the active microbolometer and the load microbolometer and between the load microbolometer and an output node of the sensor;

wherein the method comprises controlling the transistor to provide, at least in part, a coarse offset for the sensor.

17. The method of claim 9, wherein the ROIC comprises:

for each sensor in the sensor array, an active microbolometer and a load microbolometer; and a variable resistor coupled between the active microbolometer and the load microbolometer and between the load microbolometer and an output node of the sensor.

18. The method of claim 17, wherein the method comprises controlling the variable resistor to provide, at least in part, a global external resistance for the ROIC.

19. The method of claim 9, further comprising:

for each sensor in the sensor array, applying a fine offset value of a fine offset mapping to an output signal of the sensor, wherein the fine offset value and/or the fine offset mapping are ambient temperature dependent.

20. A system for performing the method of claim 9, the system comprising:

the image capture component; and a processing component configured to communicate with the ROIC and perform the method.

* * * * *